United States Patent
Choudhuri et al.

(10) Patent No.: US 6,852,859 B2
(45) Date of Patent: Feb. 8, 2005

(54) PROCESS FOR PREPARING PYRIDINIUM FLUOROCHROMATE (VI)

(75) Inventors: Mihir Kanti Choudhuri, Assam (IN); Sanjay Kumar Dehury, Assam (IN); Upasana Bora, Assam (IN); Jayashree Nath, Assam (IN); Boyapati Manoranjan Choudhary, Andhra Pradesh (IN); Lakshmi Kantam Mannepalli, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/335,102

(22) Filed: Dec. 31, 2002

(65) Prior Publication Data

US 2004/0133003 A1 Jul. 8, 2004

(51) Int. Cl.$^7$ ................................................. C07F 15/00
(52) U.S. Cl. ............................................................ 546/9
(58) Field of Search ............................................. 546/9

(56) References Cited

PUBLICATIONS

Manabendra N. Bhattacharjee, et al., "Pyridinium Fluorochromate; A New and Efficient Oxidant for Organic Substrates", Synthesis, 1982, pp. 588–590, XP001153119.

Mihir K. Chaudhuri, et al., "Easy synthesis of puridinium fluorochromate, C5H5NH[CrO3F], and its crystal structure", Journal of Fluorine Chemistry, 81 (1997) 211–213.

Manabendra N. Bhattacharjee, et al., "Pyridinium Fluorotrioxochromate(VI), (C5H5NH)[CrO3F]", Inorganic Synthesis, vol. 27, 1990, pp. 310–312, XP009012349.

Pablo Lorenzo–Luis, et al., "Fluorochromate (VI) of pyridinium" Anales de Quimica Inct. Ed., vol. 93, 1997, pp. 46–49.

International Search Report of International Application No. PCT/IB02/05535, file Dec. 16, 2002.

Primary Examiner—Cecilia J. Tsang
Assistant Examiner—Raymond Covington
(74) Attorney, Agent, or Firm—Darby & Darby

(57) ABSTRACT

The present invention relates to an economic and environmentally clean process for the preparation of the pyridinium salt of fluorotrioxo-chromate (VI), PFC, having the chemical formula $C_5H_5NH[CrO_3F]$, by direct reaction of stoichiometric amounts of hydrofluoric acid, chromium trioxide and pyridine demonstrating approxomately 100% atom economy.

21 Claims, No Drawings

PROCESS FOR PREPARING PYRIDINIUM FLUOROCHROMATE (VI)

FIELD OF THE INVENTION

The present invention relates to a process for preparing high quality pyridinium fluorochromate (VI) (PFC). More particularly, the present invention relates to a novel, economic and environmentally clean process for pyridinium salt of fluorotrioxo-chromate (VI), PFC, having the chemical formula $C_5H_5NH[CrO_3F]$, by direct reaction of stoichiometric amounts of hydrofluoric acid, chromium trioxide and pyridine demonstrating approximately 100% atom economy.

BACKGROUND OF THE INVENTION

Partial oxidations of organic substrates have always been commercially very important and for this purpose no other reagent could be as popular, as useful and as successful as the chromium (VI) reagents have been. Though there are some limitations of chromium reagents in terms of environmental antagonism, the popularity of such reagents does not seem to diminish because their performance under mild conditions with high efficiency and cost-effectiveness weigh far over their limitations. Thus, chromium (VI) based oxidizing agents have been extensively worked on leading to the development of a good number of reagents, many of which have become quite popular and performing well as oxidizing agents. Some of the important entries in the list of chromium (VI) reagents are the Collin's reagent, chromium-trioxide-3,5-dimethyl-pyrazole complex, pyridinium chlorochromate (PCC), pyridinium fluorochromate (PFC), pyridinium dichromate (PDC), quinolinium fluorochromate (QFC) and 2,2'-bipyridinium chlorochromate (BiPCC). In addition, there are a few other systems which work as reagents in combination with chromium (VI), e.g., chromium (VI)-t-butylhydroperoxide, chromium (VI)-peroxocarbonate and chromium (VI)-peroxoborate.

Pyridinium fluorochromate (PFC), in addition to being a vital reagent for several biochemically important syntheses, is a highly efficient oxidant for a wide variety of oxidative organic transformations. As oxidant, it is widely used in the oxidation of alcohols, hydroxy acids, allylic, benzylic, substituted toluenes, fused ring hydrocarbons, organic sulfides, benzyl ethers, phosphorus compounds, thioacids, substituted mandelic acids, oxidative deprotection of oximes and desilylative oxidation of alkyl trimethylsilyl ethers. PFC also acts as a very powerful oxo transfer agent such as conversion of $PPh_3$ to $OPPh_3$.

PFC successfully exercises its role as an imperative reagent for the synthesis of hydroxy ethylene, ketomethylene dipeptide isosteres, S-(+)-4-Formyl-4-Butanolide, (R)-1-benzoyloxy-3-buten-2-ol, derivatives of dimethyl penam and dimethyl penam-S, S-dioxide, sex pheromones of pink bollworm. Yet another manifestation of its versatility stems from its use for the investigations of a wide variety of reaction dynamics. Thus for instance PFC has been widely used in the kinetics and mechanistic studies of the reactions discussed above.

Pyridinium fluorochromate, often referred to as PFC is well known in the art as witnessed for example by its well deserved incorporation in the *Encyclopedia of Reagents for Organic Synthesis*, L. A. Paquette (Ed. in chief), 1995, Vol. 6, p. 4369, John Wiley and Sons, Inc., New York and *Reagents for Organic Synthesis*, M. Fieser, 1984, Vol. 11, p. 453, John Wiley and Sons, Inc., New York. Reference is made to *Synthesis*, 1982, 588; *Bull. Chem. Soc. Jpn.*, 1984, 57, 2019 and *Inorg. Synth.* 1990, 27, 310 wherein chromium trioxide is dissolved in water and aqueous hydrofluoric acid and to the solution pyridine is added. The solution is then heated to yield the crystals of PFC. The disadvantages of the procedure are the use of an excess of hydrofluoric acid and necessity of heating. Reference is made to *J. Fluorine Chem.*, 1997, 81, 211; wherein ammonium bifluoride $(NH_4HF_2)$ is dissolved in water followed by the addition of $CrO_3$ and to the clear orange solution pyridine is added. The clear orange solution is heated to yield the crystals of PFC. The disadvantage of the procedure is that the product is formed in very poor yield. Extra preparation of $NH_4HF_2$ is required adding to a relatively high cost of production.

OBJECTS OF THE INVENTION

The main object of the invention is to provide an economic, environmentally benign, and energy efficient process for the preparation of pyridinium fluorochromate, PFC which is a highly useful oxidant.

Another object of the invention is to provide a process for the preparation of pyridinium flurochromate which avoids the use of excess hydrofluoric acid or pyridine.

A further object of the invention is to provide a process for the preparation of pyridinium fluorochromate wherein the fluorotrioxochromate (VI) complex is dissolved in minimal amounts of water to avoid any loss due to solubility of the product.

It is another object of the invention to provide a process for the preparation of pyridinium fluorochromate wherein external heating is avoided by the use of an exothermic reaction.

It is a further object of the invention to provide a process for the preparation of pyridinium fluorochromate wherein 100% of atom economy is obtained, with no chromium waste being produced.

It is another object of the invention to provide a process for the preparation of pyridinium fluorochromate by a facile reaction wherein no extra steps like filtration or centrifugation are needed for isolation of the compound, the reaction is operationally simple and environmentally benign.

It is further object of the invention to provide a process for the preparation of pyridinium fluorochromate wherein the product is stable, has long shelf life, is obtained in quantitative yield, is substantially pure and crystalline without requiring recrystallization.

Yet another object of the invention is to provide a process for the preparation of pyridinium fluorochromate that is cost-effective.

SUMMARY OF THE INVENTION

Accordingly, the present invention provides an economical, environmentally benign, energy efficient process for pyridinium fluorochromate, comprising reacting chromouim(VI) oxide, hydrofluoric acid and pyridine to obtain the desired product with approximately 100% of atom economy.

In one embodiment of the invention the chromium(VI) oxide reacts with 48% hydrofluoric acid yielding the fluorotrioxochromate(VI) complex.

In another embodiment of the invention, 40% hydrofluoric acid is used instead of 48% HF.

In another embodiment of the invention use of excess hydrofluoric acid is avoided.

In another embodiment of the invention the fluorotrioxochromate(VI) complex is dissolved using minimal amount of water to avoid any loss due to solubility of the product.

In another embodiment of the invention the fluorotrioxochromate(VI) complex interacts directly with pyridine to obtain pyridinium fluorochromate, PFC.

In yet another embodiment of the invention use of excess pyridine is avoided.

In another embodiment of the invention the fluorotrioxochromate(VI) complex interacts directly with pyridine at ice-cold condition.

In yet another embodiment of the present invention no hydrofluoric acid is allowed to escape to the atmosphere, since all of it is made to react.

In yet another embodiment of the present invention no chromium waste is produced.

In another embodiment of the invention external heating is avoided since on the interaction between the fluorotrioxochromate(VI) complex with pyridine, an exothermic reaction sets in.

In still another embodiment of the present invention no extra steps like filtration or centrifugation are needed for isolation of the compound.

In yet another embodiment of the present invention the product is obtained in quantitative yield.

In still another embodiment of the present invention no waste is produced.

In yet another embodiment of the present invention the product obtained is highly pure and crystalline.

In yet another embodiment of the present invention no recrystallization is required.

In still another embodiment of the present invention the compound obtained by this protocol is very stable and has a long shelf life.

DETAILED DESCRIPTION OF THE INVENTION

The novelty of the present invention lies in the design and development of an improved process for pyridinium fluorochromate comprising the reaction of chromouim(VI) oxide, hydrofluoric acid and pyridine to afford the product approximately with 100% of atom economy. The product is very stable and cost effective. The fluoride ion does not leach during the reaction to cause the corrosion of the glass vessel used. No extraneous heating is required because the fluorotrioxochromate(VI) complex on interaction with pyridine, an exothermic reaction sets in. The reduction of the water content devoid of extraneous heating for the reaction enables 100% atom economy. The autoheating and solubility factors play vital role to achieve such unprecedented atom economy. The increasing use of PFC as a versatile oxidant attests to its credibility as a popular reagent. This reagent has not only survived the test of time but also been continuously showing newer applications. It is highly encouraging to see the width of the spectrum of the reagent. Thus as has been mentioned elsewhere, the reagent can be used for a wide variety of diverse organic transformations.

The process of the present invention comprises the reaction between chromouim(VI) oxide, hydrofluoric acid and pyridine to obtain pyridinium fluorochromate VI (PFC) in quantitative yields and with approximately with 100% of atom economy. The basic mechanism of the reaction comprises the reaction of chromium(VI) oxide with preferably 48% hydrofluoric acid to yield a fluorotrioxochromate(VI) complex. The fluorotrioxochromate(VI) complex is preferably dissolved using minimum amount of water to avoid any loss due to solubility of the product. In the alternate, the fluorotrioxochromate(VI) complex interacts directly with pyridine preferably at ice-cold conditions to obtain pyridinium fluorochromate, PFC. 40% hydrofluoric acid can also be used instead of 48% HF. no excess of hydrofluoric acid is used. Use of excess pyridine is avoided.

No extraneous heating is required because the fluorotrioxochromate(VI) complex on interaction with pyridine, an exothermic reaction sets in the above protocol demonstrates approximately 100% of atom economy. Significantly, waste such as chromium waste is not produced since the reaction proceeds with almost 100% atom economy. The reaction is facile and no hydrofluoric acid is allowed to escape to the atmosphere, since all of it is made to react. Extra steps like filtration or centrifugation are not needed for isolation of the compound. The product obtained is observed to be substantially pure and crystalline and does not require further crystallization. PFC obtained is also very stable and has a long shelf life.

Scientific Explanation

Development of Pyridinium fluorochromate is essential to overcome the practical difficulties in use of pyridinium chlorochromate, PCC, which is unfortunately quite unstable, and also many other chromium (VI) reagents. The invention resides in the discovery that replacement of Cl by F to coordinate with the Cr(VI) centre would enhance the stability of the resultant compound in addition to increasing its potential as oxidant. This is because oxidation of F to $\frac{1}{2}F_2$, unlike $Cl^-$ to $\frac{1}{2}Cl_2$, is not possible by the metal, whereas the higher electronegativity of the fluoride ion contributes to the enhancement of the electron transfer ability of the reagent. Another contributing factor to the stability of the reagent is the high propensity of fluoride to react with higher valent metal to form a stable species (HSAB concept). Thus, in a typical protocol, in the reaction between $CrO_3$ and hydrofluoric acid, chromium (VI) oxide first reacts with $F^-$ ion, in an acidic medium, to form the distorted tetrahedral fluorotrioxo-chromate(VI), $CrO_3F^-$ ion, which is then precipitated by the counter cation $C_5H_5NH^+$ ($PyH^+$), obtained by the addition of pyridine in the acidic medium. Notably in the previous method (*Synthesis* 1982, 588) a higher amount of hydrofluoric acid, than what is actually required is used. This procedure has been used world wide for the preparation of the reagent. However, the use of a relatively higher amount of HF is a matter of concern.

Previous Method

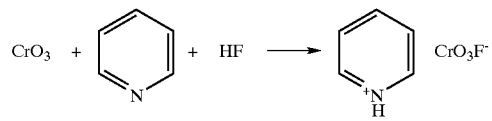

Molar ratio. 1:1:1.5

The goal of the present invention is to prepare pyridinium fluorochromate(VI) by a novel, economic and environmentally favourable improved process. The requirement of only one equivalent of fluoride and one equivalent of $H^+$ ion, with HF having no other role in the process, prompted investigation into the application of the atom economic principle to achieve the goal. Since $C_5H_5NH[CrO_3F]$ (PFC) is soluble in water, investigation was done to ascertain whether a higher yield could be obtained by the use of lesser amount of water and whether the use of a lesser amount of water would allow a relatively strong inter ionic interaction thereby making the reaction effectively more exothermic which in turn would render the extraneous heating redundant.

$$\% \text{ of atom economy} = \frac{\text{MW of atoms utilized}}{\text{MW of all the reactants used in the reaction}} \times 100$$

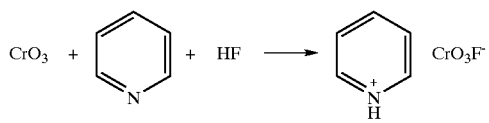

$$\% \text{ of atom economy} = \frac{199.12}{199.12} \times 100 = 100$$

The following example is given by way illustration and therefore should not be construed to limit the scope of the invention.

EXAMPLE 1
Synthesis of Pyridnium Fluorochrome

A sample of chromium(VI) oxide, $CrO_3$ (150 mmol, 15.0 g) was taken in a 250 mL polythene beaker and 48% hydrofluoric acid, HF (150 mmol, 6.253 mL) was added drop wise with continuous stirring with a Teflon rod. The stirring was continued for 8–10 min. This exercise was followed by drop wise addition of 9 mL of water under stirring over a period of 15 min leading to a clear orange colored solution. The whole was cooled in a ice-water bath for 15 min and distilled pyridine (150.02 mmol, 12.11 mL) was added drop wise to this solution with vigorous stirring. A highly exothermic reaction set in leading almost instantaneously to the formation of bright orange crystals of pyridinium fluorochromate, PFC. The whole was allowed to stand first in ice-water bath for 30 min and then at room temperature for 30 min. The compound was washed twice with hexane. The product was finally dried in vacuo over conc. $H_2SO_4$ or fused $CaCl_2$. Yield: 29.63 g (99.2%); Melting Point: 106–107° C. The chemical analyses, IR and X-ray studies of the compound match with those reported in literature. Analytical data: The compound analyzed correctly as $C_5H_6FCrNO_3$: Calc. C, 30.16; H, 3.04; N, 7.04; F, 9.54; Cr, 26.12%. Found. C, 30.1; H, 3.07; N, 6.96; F, 9.6; Cr, 26.2%.

Advantages of the Invention

The major advantages of the present invention are as follows:

1. The process is economical. No excess of reagents are used.
2. The newer methodology is environmentally clean and safe to operate.
3. In this protocol no by-product is formed.
4. The method of preparation is very facile.
5. No waste is produced.
6. No extraneous heating is required.
7. No extra purification step is required.
8. The process provides a high quality product.
9. The process is environmentally benign.

What is claimed is:

1. A process for preparing pyridinium fluorochromate VI comprising reacting chromium (VI) oxide, hydrofluoric acid and pyridine, wherein the amount of hydrofluoric acid used in the process is not an excess.
2. The process as claimed in claim 1 wherein the chromium(VI) oxide reacts with the hydrofluoric acid to yield a fluorotrioxochromate(VI) complex.
3. The process as claimed in claim 2 wherein the hydrofluoric acid used is in the form of a 40% solution of hydrofluoric acid.
4. The process as claimed in claim 2 wherein the fluorotrioxochromate(VI) complex is dissolved using a minimal amount of water.
5. The process as claimed in claim 2 wherein the fluorotrioxochromate(VI) complex interacts directly with pyridine to yield pyridinium fluorochromate, PFC.
6. The process as claimed in claim 1 wherein the use of excess pyridine is avoided.
7. The process as claimed in claim 5 wherein the interaction of the fluorotrioxochromate(VI) complex interacts directly with pyridine is carried out at ice-cold conditions.
8. The process as claimed in claim 5 wherein the interaction between the fluorotrioxochromate(VI) complex with pyridine is an exothermic reaction.
9. The process according to claim 1, wherein the hydrofluoric acid is in the form of a 48% solution of hydrofluoric acid.
10. The process according to claim 1, wherein the hydrofluoric acid is in the form of a 40% solution of hydrofluoric acid.
11. The process according to claim 2, wherein the hydrofluoric acid is in the form of a 48% solution of hydrofluoric acid.
12. The process according to claim 1, wherein no chromium waste product is produced.
13. A process for preparing pyridinium fluorochromate VI comprising
    (a) reacting chromium (VI) oxide with a stoichiometric amount of hydrofluoric acid;
    (b) adding water to dissolve the product formed in step (a); and
    (c) adding a stoichiometric amount of pyridine.
14. The process according to claim 13, wherein the hydrofluoric acid is 48%.
15. The process according to claim 13, wherein the hydrofluoric acid is 40%.
16. The process according to claim 13, wherein step (a) comprises dropwise addition of hydrofluoric acid to the chromium (VI) oxide.
17. The process according to claim 13, wherein step (b) comprises dropwise addition of water to the product formed in step (a).
18. The process according to claim 13, wherein step (c) comprises dropwise addition of pyridine.
19. The process of claim 13, wherein step (c) comprises (i) cooling the product formed in step (b) and then (ii) adding pyridine.
20. A process for preparing pyridinium fluorochromate VI comprising reacting chromium (VI) oxide, hydrofluoric acid and pyridine, without external heating.
21. A process for preparing pyridinium fluorochromate VI comprising reacting about stoichiometric amounts of chromium (VI) oxide, hydrofluoric acid and pyridine.

* * * * *